US00PP13474P2

(12) United States Plant Patent
Bradford

(10) Patent No.: US PP13,474 P2
(45) Date of Patent: Jan. 14, 2003

(54) NECTARINE TREE NAMED 'SWEET AUGUST'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/014,022

(22) Filed: Dec. 13, 2001

(51) Int. Cl.[7] ..... A01H 5/00
(52) U.S. Cl. ..... Plt./190; Plt./192
(58) Field of Search ..... Plt./190, 192

(56) References Cited

U.S. PATENT DOCUMENTS

PP6,363 P 11/1988 Bradford ..... Plt./190
PP8,947 P 10/1994 Bradford ..... Plt./189

*Primary Examiner*—Bruce R. Campell
*Assistant Examiner*—W C Haas

(57) ABSTRACT

The present invention relates to a nectarine tree, *Prunus persica,* and more particularly to a new and distinct variety broadly characterized by a medium size, vigorous, hardy, self-fertile, and productive tree that produces fruit that is uniformly large in size, sweet and subacid in flavor, globose in shape, clingstone in type, firm in texture, yellow in flesh color, and mostly red in skin color. The fruit matures under the ecological conditions described approximately the second week in August, with first picking on Aug. 8, 2001. The variety was developed as a first generation cross using 'August Snow' (U.S. Plant Pat. No. 8,947) white flesh nectarine as the selected seed parent and 'August Red' (U.S. Plant Pat. No. 6,363) yellow flesh nectarine as the selected pollen parent.

1 Drawing Sheet

BOTANICAL CLASSIFICATION

*Prunus persica.*

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'SWEET AUGUST'. The present variety was hybridized by me in 1994, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'August Snow' (U.S. Plant Pat. No. 8,947) white flesh nectarine as the selected seed parent and 'August Red' (U.S. Plant Pat. No. 6,363) yellow flesh nectarine as the selected pollen parent. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is similar to its selected seed parent, 'August Snow' (U.S. Plant Pat. No. 8,947) nectarine, by producing nectarines that are globose in shape, firm in texture, and subacid and sweet in flavor, but is distinguished therefrom and an improvement thereon by producing fruit that is clingstone instead of freestone and yellow flesh instead of white.

The present variety is most similar to its selected pollen parent, 'August Red' (U.S. Plant Pat. No. 6,363) nectarine, by producing nectarines that are mostly red in skin color, firm in texture, globose in shape, and yellow in flesh color, but is distinguished therefrom and an improvement thereon by having globose instead of reniform glands, by having a large showy blossom instead of small nonshowy, and by producing fruit that is subacid instead of acid in flavor, that is much sweeter in taste, and that matures about 10 days earlier.

DRAWING

The accompanying photograph exhibits four whole fruits positioned to display the characteristics of the skin color and form, one fruit divided transversely to the suture plane to reveal flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin County), Calif., and was developed at the state of full ripe on Sep. 12, 2001, on the original tree during its seventh growing season. All major color code designations are by reference to the Inter-Society Color Council, National Bureau of Standards. Common color names are used occasionally.

TREE

Size: Medium, reaching a height of 10' [3.05 m.] after seven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.
Form: Vase formed.
Hardiness: Hardy with respect to central California winters.
Heat tolerance: Observed to perform adequately in typical central California climatic conditions, which typically include prolonged periods of heat.
Drought tolerance: Variety is developed for commercial orchards and requires regular irrigation.
Production: Productive, thinning necessary.
Fertility: Self-fertile.
Bearing: Regular bearer with no alternate bearing observed.
Trunk:
*Size*.—Medium, reaching a maximum diameter of 4" [102 mm.] after the seventh growing season.
*Texture*.—Shaggy.
*Bark color*.—Moderate brown [58. m.Br].
*Lenticels*.—Numerous. Color: Strong orange yellow [68. s.OY]. Average Size: ⅜" [9.5 mm.].
Branches:
*Size*.—Diameter of scaffold is 1¾" [48 mm.] measured 12" above the crotch, typical of *Prunus persica,* and dependent upon cultural practices and climatic conditions.
*Texture*.—Smooth on 1st year wood, increasing roughness with age.
*Color*.—1st Year Wood Topside: Light grayish red [18. l.gy.R]. 1st Year Wood Underside: Brilliant yellow green [116. brill.YG]. Older Wood: Deep brown [56. deep Br].
*Lenticels*.—Numerous. Color: Moderate orange yellow [71. m.OY]. Average Size: 1/16" [1.6 mm.].
Leaves:
*Size*.—Medium to large. Average Length: 6¼" [159 mm.]. Average width: 1 9/16" [40 mm.].
*Arrangement*.—Alternate.
*Thickness*.—Medium.
*Form*.—Elliptical.
*Apex*.—Acuminate.
*Base*.—Acute with an average angle of eighty degrees.
*Surface*.—Smooth.
*Color*.—Dorsal Surface: Dark olive green [126. d.OlG]. Ventral Surface: Moderate yellow green [120. m.YG].
*Margin*.—Finely serrate.
*Venation*.—Pinnately net veined.
*Petiole*.—Average Length: ⅜" [9.5 mm.]. Average Thickness: 1/16" [1.6 mm.]. Color: Brilliant yellow green [116. brill.YG].
*Stipules*.—Number: 2 per leaf, up to 6 per growing tip. Average Length: ⅜" [9.5 mm.]. Color: Brilliant yellow green [116. brill.YG] when young, turning Dark Brown [59. d.Br] with age.
*Glands*.—Number: Usually 2 to 4. Position: Both oppositely and alternately positioned on the petiole and base of blade. Size: Small. Form: Globose. Color: Brilliant yellow green [116. brill.YG] turning Dark reddish orange [38. d.rO] with age.
*Leaf buds*.—Pointed.
Flower buds:
*Hardiness*.—Hardy, with respect to central California winters.
*Diameter*.—Typically ⅜" [9.5 mm.] 1 week before bloom.
*Length*.—Typically ¾" [19.1 mm.] 1 week before bloom.
*Form*.—Not appressed.
*Surface*.—Pubescent.
*Color*.—Light purplish pink [249. l.pPk].
Flowers: Perfect, complete, perigynous, usually a single pistil, typically thirty or more stamens, five sepals and petal locations alternately positioned.
*Type*.—Large, showy.
*Average flower diameter*.—1¾" [44.5 mm.].
*Number of petals*.—Usually five, very few doubles.
*Petal shape*.—Circular.
*Petal margin*.—Somewhat wavy.
*Average petal diameter*.—⅝" [15.9 mm.].
*Average petal length*.—11/16" [17.5 mm.].
*Petal apex*.—Rounded.
*Petal base*.—Rounded to slightly cordate.
*Petal color*.—Pale purplish pink [252. p.pPk] toward the apex with some Deep purplish pink [248. deep pPk] tinting near the base.
*Anther color*.—Dark red [16. d.R] when first open.
*Stigma color*.—Light yellow [86. l.Y].
*Sepal color*.—Deep purplish red [256. deep pR].
*Sepal length*.—5/32" [4 mm.].
*Sepal width*.—3/16" [5 mm.].
*Average pistil length*.—¾" [19.1 mm.].
*Average stamen length*.—⅝" [15.9 mm.].
*Fragrance*.—Moderate when nectar is present.
*Blooming period*.—Medium compared with other varieties.
*Onset of bloom*.—One percent on Feb. 26, 2001.
*Date of full bloom*.—Mar. 4, 2001.
*Duration of bloom*.—One to two weeks, dependent on ambient temperature.
*Number per cluster*.—Mostly 1, occasionally 2, rarely more than 2.

FRUIT

Maturity when described: Firm ripe, Aug. 12, 2001.
Date of first picking: Aug. 8, 2001.
Date of last picking: Aug. 22, 2001.
Size: Uniform, large.
*Average diameter axially*.—2⅞" [74 mm.].
*Average diameter across suture plane*.—2⅞" [74 mm.].
*Typical weight*.—7.4 ounces [210 grams].
Form: Uniform, symmetrical, globose.
*Longitudinal section form*.—Roundish.
*Transverse section through diameter*.—Roundish.
Suture: An inconspicuous line becoming a shallow groove very close to the apex and discontinuing slightly beyond the apex with a slight depression.
Ventral surface: Strongly rounded, slightly lipped very near the apex.
Lips: Usually equal.
Cavity: Flaring, elongated in the suture plane, suture showing on one side, Brilliant yellow [83. brill.Y] stem markings typical.
*Depth*.—⅝" [15.9 mm.].
*Breadth*.—1" [25.4 mm.].
Base: Truncate.
Apex: Rounded.
Pistil point: Both apical and oblique, slightly mammiform on some, less than ⅛" [3.2 mm.] in length.
Stem: Medium.
*Average length*.—⅜" [9.5 mm.].
*Average width*.—3/16" [4.8 mm.].
Skin:
*Thickness*.—Medium.
*Surface*.—Smooth.

*Tenacity*.—Tenacious to flesh.
*Astringency*.—Nonastringent.
*Tendency to crack*.—None observed.
*Color*.—Very dark red [17. v.d.R] to Deep red [13. deep R] over most of the surface with some Brilliant yellow [83. brill.Y] areas where sun protected and a little strong orange yellow [68. s.OY] freckling mostly on the cheeks.

Flesh:
*Color*.—Brilliant yellow [83. brill.Y] with a moderate amount of Dark red [16. d.R] streaking toward the stone and a slight amout of Moderate Red [15. m.R] flecking randomly throughout.
*Surface of pit cavity*.—Dark red [16. d.R] fibers breaking when twisted from the stone.
*Amygdalin*.—Scarce.
*Juice*.—Abundant, rich.
*Texture*.—Firm, crisp.
*Fibers*.—Abundant, fine.
*Ripens*.—Slightly earlier toward the apex.
*Flavor*.—Subacid and very sweet, ranging from 15 to 18 brix.
*Aroma*.—Slight.
*Eating quality*.—Very good.

STONE

Type: Clingstone.
Form: Oval.
Hilum: Narrow.
Base: Straight.
Apex: Acute with a rounded tip about ⅛" [3.2 mm.] long.
Sides: Equal.
Surface: Irregularly furrowed near the apex and pitted toward the base.
Ridges: Jagged toward the base.
Color: Dark brown [59. d.Br].
Average pit wall thickness: ¼" [6.4 mm.].
Average width: 15/16" [23.8 mm.].
Average length: 1⅜" [34.9 mm.].
Average breadth: 11/16" [17.5 mm.].
Kernel:
*Form*.—Oval.
*Pellicle color*.—Light brownish gray [63. l.brGy].
*Skin color*.—Light yellow [86. l.Y] when first removed.
*Vein color*.—Light brownish gray [63. l.brGy].
*Taste*.—Bitter.
*Viable*.—Yes.
*Average width*.—½" [12.7 mm.].
*Average length*.—¾" [19.1 mm.].
*Amygdalin*.—Abundant.

USE

Market: Fresh market and long distance shipping.
Keeping quality: Good. Fruit quality observed to remain in good condition in after 17 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its selected pollen parent, 'August Red' (U.S. Plant Pat. No. 6,363) nectarine, by producing nectarines that are mostly red in skin color, firm in texture, globose in shape, and yellow in flesh color, but is distinguished therefrom and an improvement thereon by having globose instead of reniform glands, by having a large showy blossom instead of small nonshowy, and by producing fruit that is subacid instead of acid in flavor, that is sweeter in taste, and that matures about 10 days earlier.

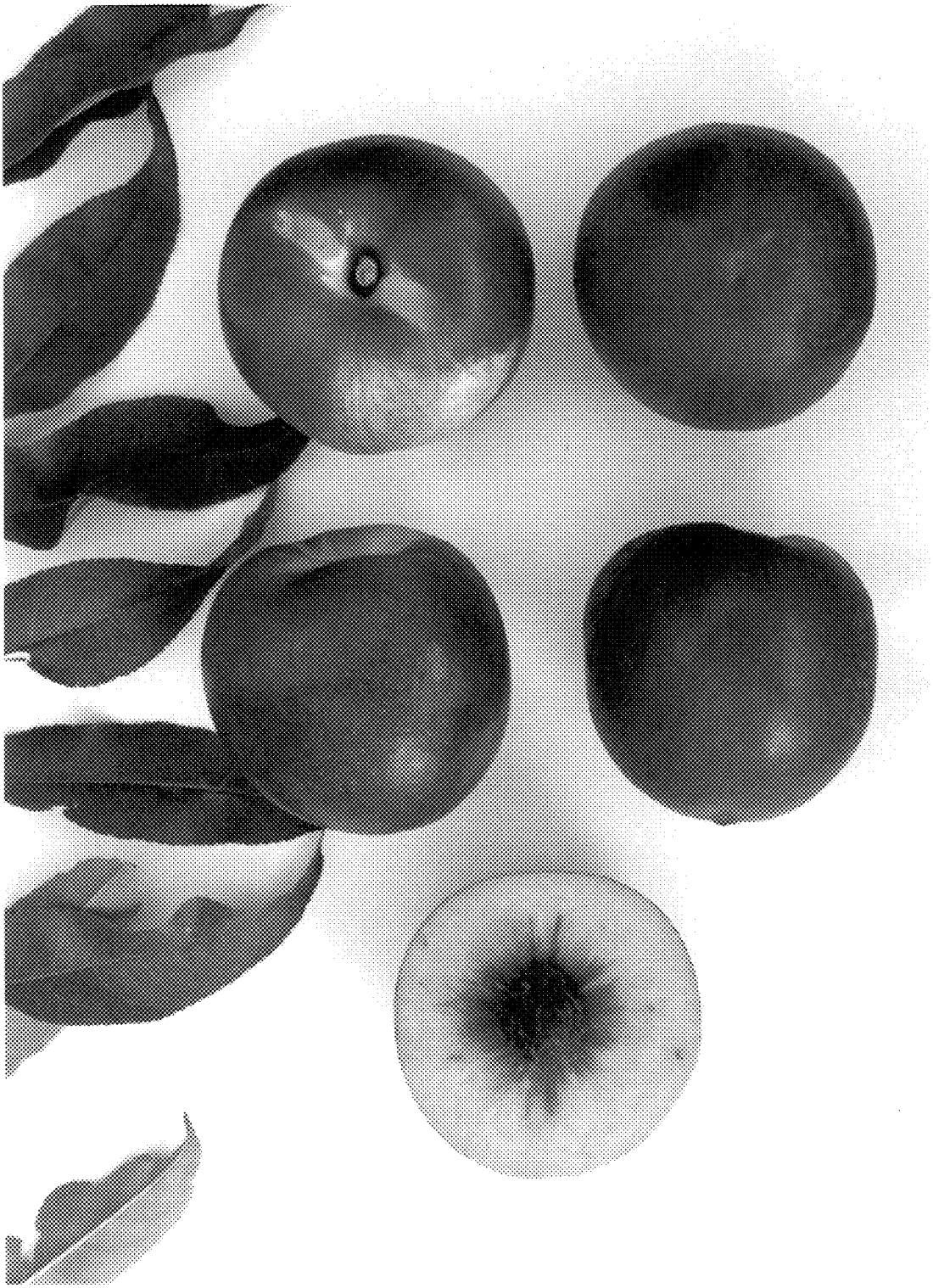

* * * * *